United States Patent
Brandenburg et al.

(10) Patent No.: US 8,263,788 B2
(45) Date of Patent: Sep. 11, 2012

(54) METHOD FOR THE PRODUCTION OF 1,3-DIOXOLANE-2-ONES AND CARBOXYLIC ACID ESTERS BY MEANS OF TRANSACYLATION IN BASIC REACTION CONDITIONS

(75) Inventors: Joerg Brandenburg, Wiesbaden (DE); Rolf Dach, Gau-Algesheim (DE); Hanfried Baltes, Woellstein (DE)

(73) Assignee: Boehringer Ingelheim Pharma GmbH & Co. KG, Ingelheim am Rhein (DE)

( * ) Notice: Subject to any disclaimer, the term of this patent is extended or adjusted under 35 U.S.C. 154(b) by 145 days.

(21) Appl. No.: 12/677,920

(22) PCT Filed: Sep. 3, 2008

(86) PCT No.: PCT/EP2008/061618
§ 371 (c)(1),
(2), (4) Date: May 14, 2010

(87) PCT Pub. No.: WO2009/037111
PCT Pub. Date: Mar. 26, 2009

(65) Prior Publication Data
US 2010/0305146 A1    Dec. 2, 2010

(51) Int. Cl.
*C07D 409/00* (2006.01)
*C07D 491/00* (2006.01)
*C07D 491/08* (2006.01)

(52) U.S. Cl. .............. 549/59; 546/19; 546/91

(58) Field of Classification Search .......... 549/59; 546/19, 91
See application file for complete search history.

Primary Examiner — Nizal Chandrakumar

(74) *Attorney, Agent, or Firm* — Michael P. Morris; Wendy A. Petka

(57) ABSTRACT

The invention relates to a method for producing 1,3-dioxolane-2-ones of general formula (3) in basic reaction conditions by reesterifying the respective ester of general formula (1) in which R1 to R5 have the meanings indicated in the claims and the description. The invention further relates to a method for producing 2-hydroxy carboxylic acid esters of general formula (5) with or without isolation of the intermediate in the form of a derivative of the 1,3-dioxolane-2-one of general formula (3) in basic reaction conditions by reesterifying the respective ester of general formula (1) in which R1, R2, and R6 have the meanings indicated in the claims and the description. The method according to the invention allows the reaction to take place in very gentle basic conditions, causing fewer secondary reactions and providing a greater yield than reactions in highly polar aprotic solvents. Acid-sensitive and/or temperature-sensitive compounds can be synthesized.

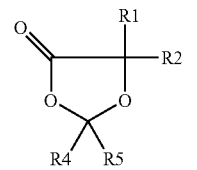

3

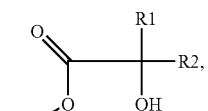

1

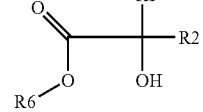

5

18 Claims, No Drawings

METHOD FOR THE PRODUCTION OF 1,3-DIOXOLANE-2-ONES AND CARBOXYLIC ACID ESTERS BY MEANS OF TRANSACYLATION IN BASIC REACTION CONDITIONS

RELATED APPLICATIONS

This application is a 371 of International Application No. PCT/EP2008/061618, filed Sep. 3, 2008, which claims priority to European Patent Application No. 07116371.1, filed Sep. 13, 2007, the contents of which are incorporated herein by reference in their entirety.

TECHNICAL FIELD OF THE INVENTION

The invention relates to a process for preparing 1,3-dioxolan-2-ones of general formula 3

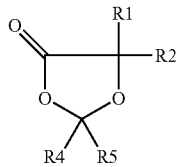

under basic reaction conditions by transesterification of the corresponding ester of general formula 1,

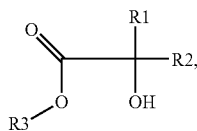

wherein $R_1$ to $R_5$ have the meanings given in the claims and specification. The invention further relates to a process for preparing 2-hydroxycarboxylic acid esters of general formula 5

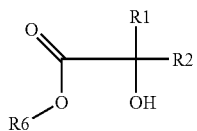

with or without isolation of the intermediate in the form of a derivative of the 1,3-dioxolan-2-one of general formula 3 under basic reaction conditions by transesterification of the corresponding ester of general formula 1, wherein $R_1$, $R_2$ and $R_6$ have the meanings given in the claims and specification.

The process according to the invention allows a reaction to be carried out under very mild basic conditions, which unlike reactions in highly polar aprotic solvents produce fewer side reactions and give a higher yield. It is possible to synthesise acid- and/or temperature-sensitive compounds.

The combination of zeolite type 4a and tert.-alkoxide catalyses transesterification reactions with scopine without any appreciable rearrangements resulting in scopoline taking place.

BACKGROUND TO THE INVENTION

Acetonides or derivatives of 1,3-dioxolane are cyclic ketals which are prepared for example from 1,2-diols, ketones or aldehydes. It is known in the prior art that acid catalysts assist and/or enable this reaction. The cyclic ketals are synthetically valuable compounds which may be used to good effect on account of their special properties.

In the special case of the 1,3-dioxolan-2-ones, for example the carboxylic acid function structurally contained therein may be activated to assist acylation reactions. As in this case possibly volatile ketones or aldehydes escape as a by-product of the reaction, the reaction equilibrium is favourably influenced towards the acylation of an alcohol, for example (cf. "A new Synthesis of alpha-Hydroxycarboxylates and 2-Hydroxybenzoates", Khalaj, Ali; Aboofazaeli, Rem; Iranian Journal of Chemistry & Chemical Engineering (1997), 16(1), 1-3). 1,3-Dioxolan-2-ones, by cyclisation of an alpha-hydroxycarboxylic acid, combine the protection of their individual functionalities and convert them into an ether and a lactone functionality in each case. This sometimes decisively increases the stability of the whole molecule. Depending on the pattern of substituents and the intended reaction, either the stabilising or the activating effect in the molecule may dominate and be exploited.

It is possible to use ketones and aldehydes as the protective group for alpha-hydroxycarboxylic acids, as the former can be cleaved again from the 1,3-dioxolan-2-ones under defined mild conditions (acidic or basic).

1,3-dioxolan-2-ones are also known starting materials for preparing alpha-hydroxycarboxylic acid esters and alpha-hydroxycarboxylic acid amides ("Synthesis of alpha-Hydroxycarboxamides from Acetonids of alpha-Hydroxycarboxylicacids and Primary Amines", Khalaj, A.; Nahid, E., Synthesis (1985), (12), 1153-1155).

Methods of synthesis for preparing dioxolanes are described for example in "Synthesis and Configuration of Aryl-Substituted 1,3-Dioxolan-4-ones", Samoiloski, N. A.; Lapkin, L I.; Proshutinski, V. I.; Krutko, N. E.; Zhurnal Organicheskoi Khimii (1973), 9(6), 1145-1148. The cleaving of 1,3-dioxolan-2-ones to form the 2-hydroxycarboxylic acid ester has already been described in the literature (cf. "A new Synthesis of alpha-Hydroxycarboxylates and 2-Hydroxybenzoates", Khalaj, Ali; Aboofazaeli, Reza; Iranian Journal of Chemistry & Chemical Engineering (1997), 16(1), 1-3). The cleaving may be carried out with acid or base catalysis.

Furthermore, numerous 2-hydroxycarboxylic acid esters are known for their pharmacological activity, with the result that there is a constant search for ways of developing better and simpler methods of synthesising them. It is also known that alpha-hydroxycarboxylic acid esters themselves may be used as precursors for preparing other pharmacologically active compounds. One example of this is the pharmacologically effective 2,2-diarylglycolic acid esters of aminoalcohols, such as e.g. the tiotropium salt having the chemical formula:

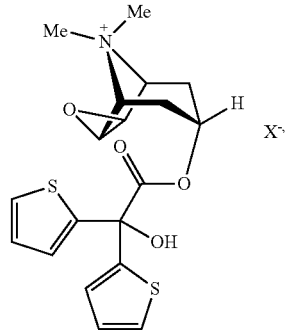

wherein X⁻ denotes an anion, preferably bromide. Tiotropium salts are categorised as anticholinergics. In the prior art tiotropium bromide in particular is described as a highly potent anticholinergic. Tiotropium bromide is known for example from EP 418 716 A1.

All the preparation methods for acetonides/dioxolanones published hitherto use strong acids as catalysts. A problem of the known processes is therefore that acid-sensitive compounds cannot be obtained using the known conventional acid-catalysed methods of synthesis. This restricts the use of the reaction to acid-stable raw materials and target molecules. In a reaction with thienyl-substituted glycolic acid, for example, conventional methods of preparation cannot be used owing to the instability of this component. A great many side reactions are obtained, in some cases with the formation of coloured components which contaminate the end product and incur considerable expense in purification.

The problem on which the present invention is based is therefore to provide an improved mild, technically practicable method of synthesis which provides a way of synthesising 1,3-dioxolanes or 2-hydroxycarboxylic acid esters that have temperature- and/or acid-sensitive functionalities.

DESCRIPTION OF THE INVENTION

In a first aspect the present invention relates to a process (reaction 1a) for preparing 1,3-dioxolan-2-one of formula 3

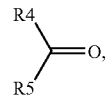

3 wherein
$R_1$ and $R_2$ each independently of one another represent hydrogen or a cycloalkyl, aryl or heteroaryl group, while the cycloalkyl, aryl or heteroaryl group may optionally be mono- or polysubstituted in each case;
$R_4$ and $R_5$ are each independently of one another selected from among hydrogen, $C_1$-$C_6$-alkyl, or $R_4$ and $R_5$ together form a saturated or mono- or polyunsaturated carbocyclic or heterocyclic ring which may contain one or more heteroatoms, selected from S, N or O, each of which may optionally be mono- or polysubstituted independently of one another, while $R_4$ and $R_5$ cannot both simultaneously be hydrogen;
while a 2-hydroxycarboxylic acid ester of formula 1

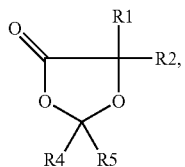

1 wherein
$R_1$ and $R_2$ are as hereinbefore defined and
$R_3$ denotes methyl, ethyl, propyl, isopropyl, isopropenyl, butyl, N-succinimide, N-phthalimide, phenyl, nitrophenyl, fluorophenyl, pentafluorophenyl, vinyl, 2-allyl, is reacted, in a suitable solvent with the addition of a suitable basic catalyst, preferably a catalyst selected from among the tert.-alkoxides, in the presence of zeolite, in one step, with a compound of formula 2

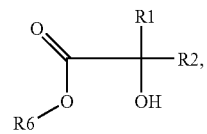

2 wherein $R_4$ and $R_5$ are as hereinbefore defined.

In a second aspect the invention further relates to a process (reaction 1a+reaction 1b) for preparing a compound of formula 5

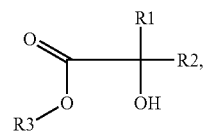

5 wherein
$R_1$ and $R_2$ are as hereinbefore defined;
$R_6$ denotes an organic group,
wherein a 2-hydroxycarboxylic acid ester of formula 1

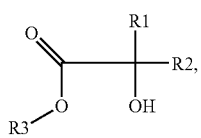

1 wherein
$R_1$ and $R_2$ are as hereinbefore defined;
$R_3$ is different from $R_6$ and is selected from among methyl, ethyl, propyl, isopropyl, isopropenyl, butyl, N-succinimide, N-phthalimide, phenyl, nitrophenyl, fluorophenyl, pentafluorophenyl, vinyl, 2-allyl, is reacted in a first step in a suitable solvent, with the addition of a suitable basic catalyst, preferably a catalyst selected from among the tert. alkoxides, in the presence of zeolite, in one step, with a compound of formula 2

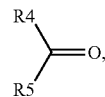

2 wherein $R_4$ and $R_5$ are as hereinbefore defined,
to form a compound of formula 3

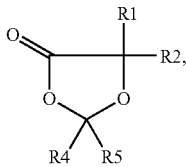
3 wherein $R_1$, $R_2$, $R_4$ and $R_5$ have the meanings given above,
and wherein
the compound of formula 3 is reacted in a second step (reaction 1b) in a suitable solvent, with the addition of a suitable basic catalyst, preferably a catalyst selected from among the tert. alkoxides, in the presence of zeolite, with a compound of formula 4

4, wherein
$R_6$ denotes an organic group which is different from $R_3$,
to form a compound of formula 5.

In a third aspect the invention further relates to a process (reaction 2) for preparing a compound of formula 5

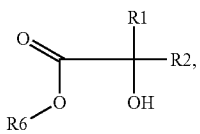
5 wherein
$R_1$ and $R_2$ are as hereinbefore defined and
$R_6$ is as hereinbefore defined;
wherein a 2-hydroxycarboxylic acid ester of formula 1

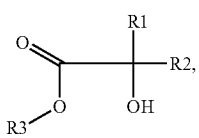
1 wherein
$R_1$ and $R_2$ and $R_3$ are as hereinbefore defined;
is reacted in one step (reaction 2) with a compound of formula 2, particularly acetone, which acts as solvent, and a compound of formula 4

4, wherein
$R_6$ denotes an organic group that is different from $R_3$,
with the addition of a suitable basic catalyst, preferably a catalyst selected from among the tert. alkoxides, in the presence of zeolite, to form a compound of formula 5.

DETAILED DESCRIPTION OF THE INVENTION

Definitions of Terms

The term "aryl" or "aryl group" denotes a 6- to 10-membered aromatic carbocyclic group and includes for example phenyl and naphthyl. Other terms that contain the component "aryl" have the same meaning for the aryl part. Examples of these components are: arylalkyl, aryloxy or arylthio.

The term "heteroaryl" or "heteroaryl group" denotes a stable 5- to 8-membered, preferably 5- or 6-membered monocyclic or 8- to 11-membered bicyclic aromatic heterocyclic group. Each heterocyclic group consists of carbon atoms and 1 to 4 heteroatoms, selected from nitrogen, oxygen and sulphur. Examples of heteroaryls are: pyridyl, pyrimidinyl, pyrazinyl, pyridazinyl, pyrrolyl, imidazolyl, pyrazolyl, thienyl, furanyl, isoxazolyl, isothiazolyl, oxazolyl, thiazolyl, oxadiazolyl, thiadiazolyl, quinolinyl, isoquinolinyl, indolyl, benzimidazolyl, benzofuranyl, benzoxazolyl, benzisoxazolyl, benzopyrazolyl, benzothiofuranyl, benzothiazolyl, quinazolinyl, indazolyl, or condensed heteroaryl such as cyclopentenopyridine, cyclohexanopyridine, cyclopentanopyrimidine, cyclohexanopyrimidine, cyclopentanopyrazine, cyclohexanopyrazine, cyclopentanopyridazine or also cyclohexanopyridazine.

The terms "alkyl" and "alkyl groups" as well as alkyl groups which are part of other groups denote branched and unbranched alkyl groups with 1 to 6 carbon atoms. Examples include: methyl, ethyl, propyl, butyl, pentyl, hexyl. Unless stated otherwise, the above-mentioned terms propyl, butyl, pentyl and hexyl include all the possible isomeric forms. For example the term propyl includes the two isomeric groups n-propyl and iso-propyl, the term butyl denotes the isomeric groups n-butyl, iso-butyl, sec. butyl and tert.-butyl.

The terms "alkoxy" or "alkyloxy groups" denote branched and unbranched alkyl groups with 1 to 6 carbon atoms which are linked via an oxygen atom. Examples include: methoxy, ethoxy, propoxy, butoxy, pentoxy, hexoxy. Unless stated otherwise, the above-mentioned terms include all the possible isomeric forms.

Terms such as "fluorophenyl" and "nitrophenyl" denote phenyl rings substituted by fluorine or $NO_2$. These include all the possible isomers (ortho, meta or para), while para- and meta-substitution are of particular importance.

The terms "carbocyclic ring" or "cycloalkyl groups" denote cycloalkyl groups with 3 to 6 carbon atoms, for example cyclopropyl, cyclobutyl, cyclopentyl or cyclohexyl.

By the term "heterocyclic group" is meant a stable 5- to 8-membered, but preferably 5- or 6-membered monocyclic or 8- to 11-membered bicyclic heterocyclic group, which is either saturated or unsaturated and may also be aromatic, if this is chemically possible in the circumstances. Each heterocyclic group consists of carbon atoms and 1 to 4 heteroatoms, selected from nitrogen, oxygen and sulphur. Examples of heterocyclic groups are pyrrolinyl, pyrrolidinyl, pyrazolinyl, pyrazolidinyl, 1,2,5,6-tetrahydropyridinyl, piperidinyl, morpholinyl, thiomorpholinyl, pyranyl, thiopyranyl, piperazinyl, indolinyl or also 1,2,3,3a,4,6a-hexahydrocyclopenta[c]pyrrolyl.

The terms "nitrogen" and "sulphur" and the respective element symbols encompass every oxidised form thereof and also quaternary forms of a basic nitrogen atom.

Preferred Embodiments

The process variants according to the invention are hereinafter described in detail. They are represented in the following Reaction Scheme 1:

Reaction Scheme 1

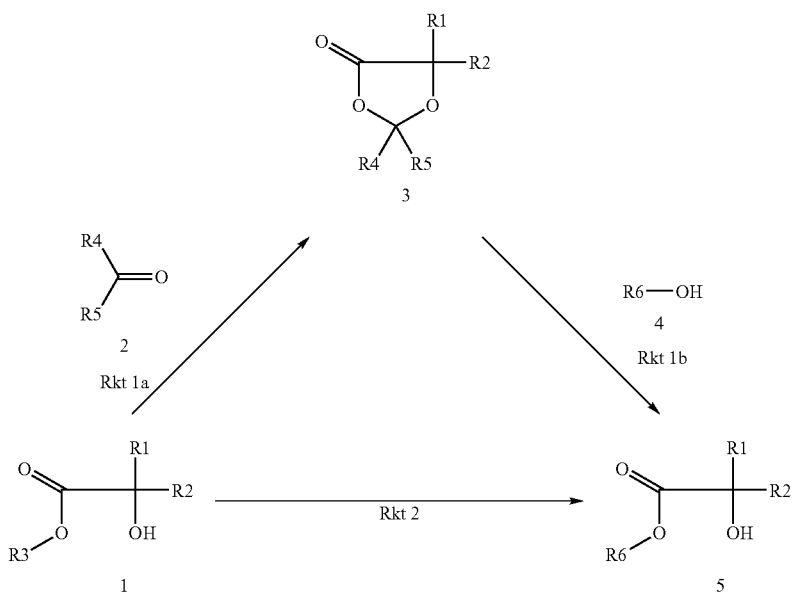

The groups $R_1$ to $R_6$ are defined as hereinbefore.

Reaction 1a: The process according to the invention (reaction 1a) according to the first aspect of the invention relates to the reaction of a 2-hydroxycarboxylic acid ester of general formula 1 with a compound of formula 2 to form a 1,3-dioxolan-2-one of general formula 3. This is shown in the following Reaction Scheme 2:

Reaction Scheme 2

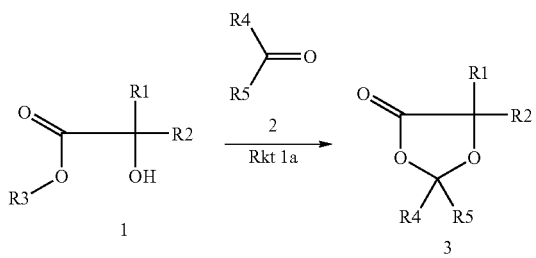

The groups $R_1$ to $R_5$ are defined as hereinbefore.

According to a particularly preferred embodiment of the invention $R_3$ is preferably selected from methyl, ethyl, propyl and butyl, particularly preferably methyl.

Particularly preferably, $R_1$ and $R_2$ are each selected from a heteroaryl group which may optionally be mono- or polysubstituted in each case. Preferred substituents are halogen atoms, such as fluorine, chlorine, bromine or iodine, —CN, $C_1$-$C_4$-alkyl, $C_1$-$C_4$-alkoxy, hydroxy or $CF_3$. Most particularly preferably, $R_1$ and $R_2$ both represent the same heteroaryl group, and in particular $R_1$ and $R_2$ are both thienyl groups.

Preferably $R_4$ and $R_5$ are independently selected from $C_1$-$C_6$-alkyl, particularly preferably methyl, ethyl, butyl or pentyl. According to a preferred embodiment $R_4$ and $R_5$ both represent the same group, but cannot both simultaneously be hydrogen, and particularly preferably $R_4$ and $R_5$ are both methyl.

According to another preferred embodiment $R_4$ and $R_5$ together form a saturated or unsaturated carbocyclic or heterocyclic ring. The carbocyclic ring is preferably selected from cyclohexyl and cyclopentyl. The heterocyclic group is preferably selected from piperidinyl, quinuclidinyl, tropinyl and pyrrolidinyl, in each case optionally substituted by one or more substituents. These are preferably selected from halogen atoms, such as fluorine, chlorine, bromine or iodine, —CN, $C_1$-$C_4$-alkyl, $C_1$-$C_4$-alkoxy, hydroxy, $CF_3$ and —O—COR', where R' denotes a group selected from among $C_1$-$C_4$-alkyl, benzyl and phenylethyl, which may optionally be substituted in each case by hydroxy, hydroxymethyl or methoxy, and particularly preferably $R_4$ and $R_5$ together form a pyridinyl ring.

When $R_4$ and $R_5$ form a ring system, an aromatic carbocyclic or heterocyclic ring may also be formed in the compound of formula 2. Examples include benzyl, pyrrole, furan and thiophene. After the reaction of the compound of formula 2 to form the 1,3-dioxolan-2-one the ring system loses its aromatic nature on account of the bridging carbon atom between the two cyclic oxygens of the dioxolane.

According to a particularly preferred embodiment of the invention $R_4$ and $R_5$ form together with a nitrogen atom (also possible as a quaternary ammonium salt) a heterocyclic ring selected from pyrrole, pyrroline, pyrrolidine, pyridine, piperidine, morpholine,

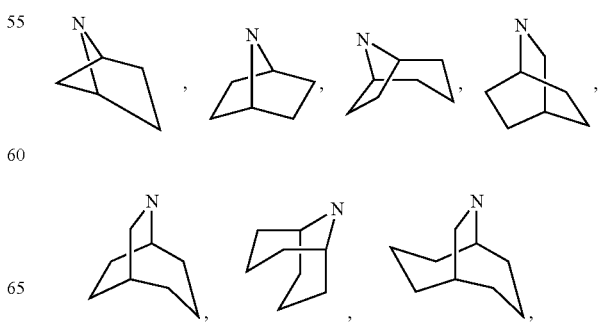

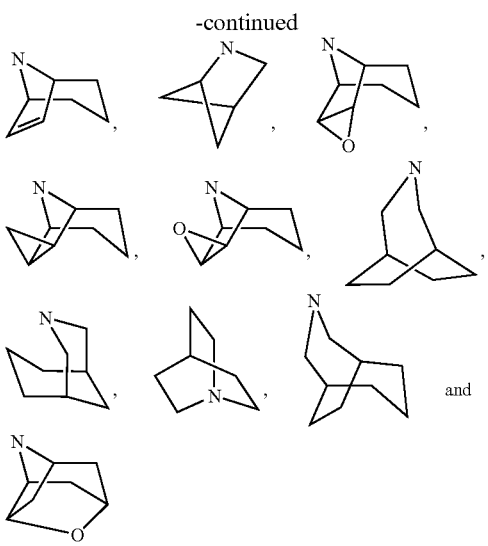

which may optionally be substituted by one or more groups, preferably a group selected from among OH, F, methyl, ethyl, methoxy and —O—COR', where R' denotes a group selected from among $C_1$-$C_4$-alkyl, benzyl and phenylethyl, which may be substituted in each case by hydroxy, hydroxymethyl or methoxy.

The compounds of formula 2 are not particularly restricted; known ketones or aldehydes may be used, provided that they do not interfere with the formation of a 1,3-dioxolan-2-one. Sterically particularly demanding groups are therefore not preferred. Examples of ketones include cyclohexanone and acetone. Examples of aldehydes include isobutyraldehyde, benzaldehyde, N-methyl-1,4-piperidone, tropanone, piperidone and quinuclidinone.

A particularly mild reaction is possible according to the invention because the catalyst, preferably a catalyst selected from among the tert. alkoxides, is used together with a zeolite. By tert.-alkoxides are meant alkoxides that contain sterically demanding alkyl groups, in which there is at least one quaternary carbon centre. By quaternary carbon centres are meant carbon centres which do not carry a hydrogen atom, but are substituted by 3 to 4 alkyl groups. Carbon centres that are substituted by 3 alkyl groups preferably carry the alkoxide group as the fourth substituent. Suitable tert.-alkoxides are preferably alkali or alkaline earth metal alkoxides, particularly preferably sodium or potassium-tert.-butoxide or sodium- or potassium-tert.-amylate.

Particularly preferred zeolites are molecular sieves which are selected from among the molecular sieves of a basic nature, consisting of alkali or alkaline earth-containing alumosilicates, such as sodium or potassium-containing alumosilicates, preferably molecular sieves with the empirical formula $Na_{12}[(AlO_2)_{12}(SiO_2)_{12}] \times H_2O$ or $Na_{12}Al_{12}Si_{12}O_{36} \times nH_2O$, where n is preferably ≤6, type 4A molecular sieves being particularly preferred according to the invention.

The reaction of the compound of formula 1 with the compound of formula 2 to obtain the compound of formula 3 is preferably carried out in solution. The solution obtained is generally stirred until the reaction is complete. The work may be done at ambient temperature (approx. 23° C.) or optionally also at slightly elevated temperature in the range from 25-50° C. This depends on the reactants and on the type of catalyst chosen. The reaction takes place under basic reaction conditions and also functions at ambient temperature and below.

Preferably the reaction takes place under mild conditions at a temperature of about 30° C., particularly preferably in the range from about 0 to about 30° C.

The solvents that may be used are preferably aprotic organic solvents, preferably weakly polar organic solvents. The solvents used according to the invention are particularly preferably acetone, pyridine, acetonitrile and tetrahydrofuran, while acetone, acetonitrile and tetrahydrofuran are preferred. It may be of particular advantage if the compound of formula 2 can act simultaneously as reactant and solvent. This is the case for example when acetone is used as the compound of formula 2 and is particularly advantageous if the alpha-hydroxycarboxylic acid ester of formula 1 is soluble in this solvent.

The solution obtained is generally stirred until the reaction is complete. After the reaction has ended the compounds of formula 3 are isolated from the solution. The products obtained may, if necessary, be purified by recrystallisation from a suitable solvent. The product obtained is isolated and optionally dried in vacuo.

The process according to the invention (reaction 1a) is carried out selectively, with side reactions largely being suppressed.

According to a particularly preferred embodiment of the invention the process according to the invention produces 1,3-dioxolan-2-ones with a type A basic structure and 1,3-dioxolan-2-ones with a type B basic structure:

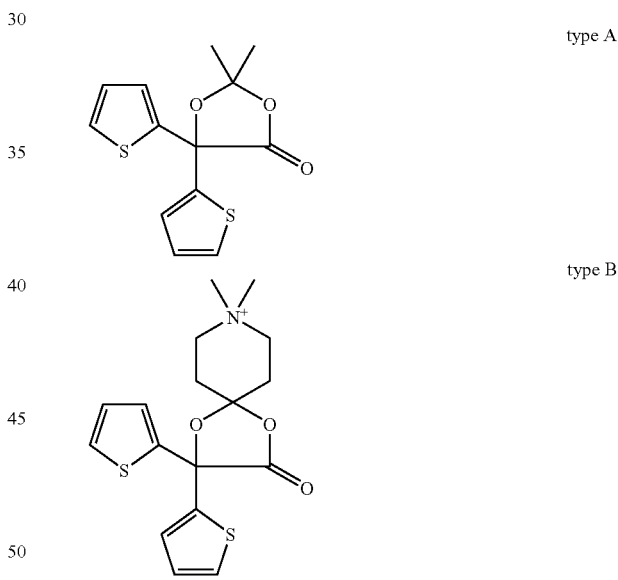

It has not hitherto been possible to prepare these basic structures of type A and type B by a conventional acid-catalysed process (cf. "Synthesis and Selective Activity of Cholinergic Agents with Rigid Skeletons", Shoji Takemura, Yasuyoshi Miki, Mariko Hoshida, Mayumi Shibano, Aritomo Suzuki; Chem. Pharm. Bull. 29(10) 3019-3025 (1981)), as they and their dithienylglycolic acid precursors are acid-sensitive. Therefore, compounds of this kind can now be obtained using the process according to the invention.

The present invention therefore also relates to a process for preparing acid-sensitive 2-hydroxycarboxylic acid esters 5, in which an acid-sensitive 2-hydroxycarboxylic acid ester 1 may also be present as starting material.

1,3-dioxolan-2-ones of type B surprisingly act as anticholinergics on the muscarinic receptor, in a similar manner to tiotropium salts, and may be used therapeutically to treat certain diseases. Particular mention may be made for example of the treatment of asthma or COPD (chronic obstructive pulmonary disease). Pharmacologically active benzilic acid and mandelic acid analogues have been described for example in "Synthesis and Selective Activity of Cholinergic Agents with Rigid Skeletons", Shoji Takemura, Yasuyoshi Miki, Mariko Hoshida, Mayumi Shibano, Aritomo Suzuki; Chem. Pharm. Bull. 29(10) 3019-3025 (1998)).

In particular the compounds of formula 610:

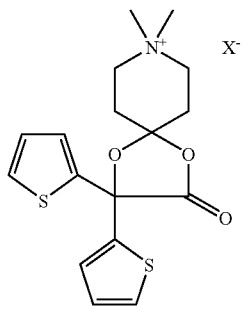

610 wherein $X^-$ denotes an anion with a single charge are highly potent anticholinergic active substances. For example this anion may be chloride, bromide, iodide, sulphate, phosphate, methanesulphonate, nitrate, maleate, acetate, citrate, fumarate, tartrate, oxalate, succinate, benzoate or p-toluenesulphonate.

Accordingly, in another aspect, the present invention relates to the compounds of formula 610 wherein $X^-$ denotes chloride, bromide, iodide, sulphate, phosphate, methanesulphonate, nitrate, maleate, acetate, citrate, fumarate, tartrate, oxalate, succinate, benzoate or p-toluenesulphonate, the substituents on the nitrogen being selected from among methyl, ethyl, n-alkyl, iso-alkyl, alkoxyalkyl, hydroxyalkyl, and the thienyl groups may optionally have one or more substituents which are selected from among fluorine, chlorine, bromine, iodine, —CN, $C_1$-$C_4$-alkyl, $C_1$-$C_4$alkoxy, hydroxy and $CF_3$.

Other uses of 1,3-dioxolan-2-one compounds that may be prepared according to the invention are for example in the field of synthesis, for preparing pharmacologically active carboxylic acid esters, such as e.g. tiotropium bromide. This may be done for example from or via compounds of type A as described above.

1,3-dioxolan-2-ones may be used particularly when acid-sensitive compounds are present, such as acid-sensitive carboxylic acid esters, e.g. methyl 2,2-dithienylglycolate. In addition, the 1,3-dioxolan-2-ones may again be converted into other (e.g. pharmacologically active) carboxylic acid esters or carboxylic acid salts.

The process according to the invention (reaction 1a) makes it possible to carry out a reaction under very mild conditions which have fewer side reactions and consequently a higher yield than reactions in highly polar aprotic solvents. It may be used for example for synthesising delicate acid-unstable and/or temperature-sensitive systems.

Reaction 1b

The process according to the invention (reaction 1b) further relates to the preparation of 2- or alpha-hydroxycarboxylic acid esters of general formula 5 starting from a 1,3-dioxolan-2-one of general formula 3 under basic reaction conditions. Reactions of this kind are known from the prior art. This is illustrated in the following Reaction Scheme 3:

Reaction Scheme 3

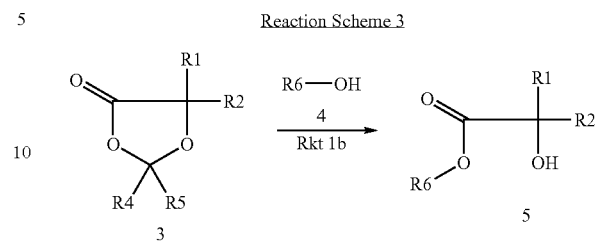

The groups $R_1$ to $R_6$ are defined as hereinbefore.

According to the invention the compound of formula 3 is preferably reacted in one step (reaction 1b) in a suitable solvent with the addition of a suitable basic catalyst, preferably a catalyst selected from among the tert. alkoxides, in the presence of zeolite, with a compound of formula 4

$$R_6\text{—O—H},\qquad 4$$

wherein $R_6$ denotes an organic group which is different from $R_3$, to form a compound of formula 5

5 wherein $R_1$, $R_2$ and $R_6$ have the meanings given above.

The reaction temperature depends on the reactants and on the type of catalyst chosen. The reaction takes place under basic reaction conditions and also functions at ambient temperature and below. Preferably the reaction takes place under mild conditions at a temperature of about 30° C., particularly preferably in the range from about 0 to about 30° C.

The solvents that may be used are preferably aprotic organic solvents, preferably weakly polar organic solvents. The solvents used according to the invention are particularly preferably acetone, pyridine, acetonitrile and tetrahydrofuran, while acetone, acetonitrile and tetrahydrofuran are particularly preferred.

For further details reference is made for example to "A new Synthesis of alpha-Hydroxycarboxylates and 2-Hydroxybenzoates", Khalaj, Ali; Aboofazaeli, Reza; Iranian Journal of Chemistry & Chemical Engineering (1997), 16(1), 1-3.

Reaction 2

The process according to the invention (reaction 2) also relates to the preparation of 2-hydroxycarboxylic acid esters of general formula 5 via an intermediate in the form of a derivative of the 1,3-dioxolan-2-one of general formula 3 under basic reaction conditions by transesterification of the corresponding ester of general formula 1. The 1,3-dioxolan-2-one of formula 3 is not isolated as an intermediate product in this case but further processed directly to form the new ester. This is shown in the following Reaction Scheme 4:

Reaction Scheme 4

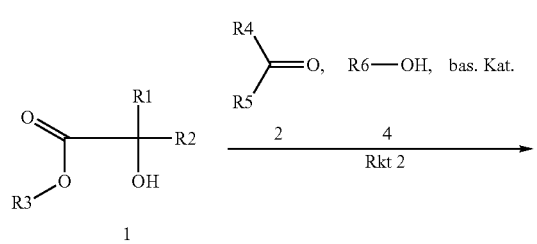

The groups $R_1$ to $R_6$ are defined as hereinbefore.

Here, a transesterification or transacylation of the ester takes place under basic reaction conditions.

If the intermediate product is to be isolated in the form of the 1,3-dioxolan-2-one of formula 3, the procedure used is as described hereinbefore in reaction 1a (reaction 1a->intermediate product is isolated->reaction 1b), which may be followed by reaction 1b.

If, however, the intermediate product is to be isolated in the form of the 1,3-dioxolan-2-one of formula 3, the process according to the invention (reaction 2) is preferably carried out in one step (reaction 1a+reaction 1b=reaction 2). For this, the compound of formula 1 is reacted using the compound of formula 2 and the compound of formula 4 is reacted virtually in one step ("one pot process") to form a compound of formula 5.

Obviously, reaction 1a and reaction 1b, as described hereinbefore, may also be carried out successively, without isolating the intermediate product; however, this is less preferable.

According to a particularly preferred embodiment of the invention $R_3$ is preferably selected from methyl, ethyl, propyl and butyl, particularly preferably methyl or ethyl.

Particularly preferably $R_1$ and $R_2$ are in each case selected from a heteroaryl group which may optionally be mono- or polysubstituted in each case. Preferred substituents are halogen atoms, such as fluorine, chlorine, bromine or iodine, —CN, $C_1$-$C_4$-alkyl, $C_1$-$C_4$-alkoxy, hydroxy or $CF_3$. Most particularly preferably $R_1$ and $R_2$ both represent the same heteroaryl group, and in particular $R_1$ and $R_2$ are both thienyl groups.

According to a particularly preferred embodiment of the invention $R_4$ and $R_5$ form, together with a nitrogen atom, a heterocyclic ring selected from pyrrole, pyrroline, pyrrolidine, pyridine, piperidine, morpholine, quinuclidine

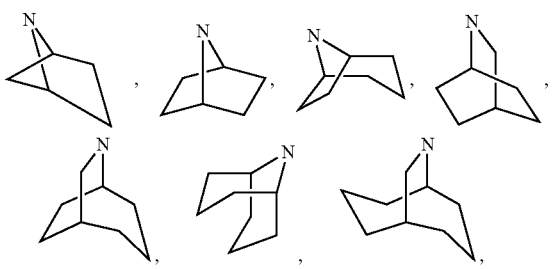

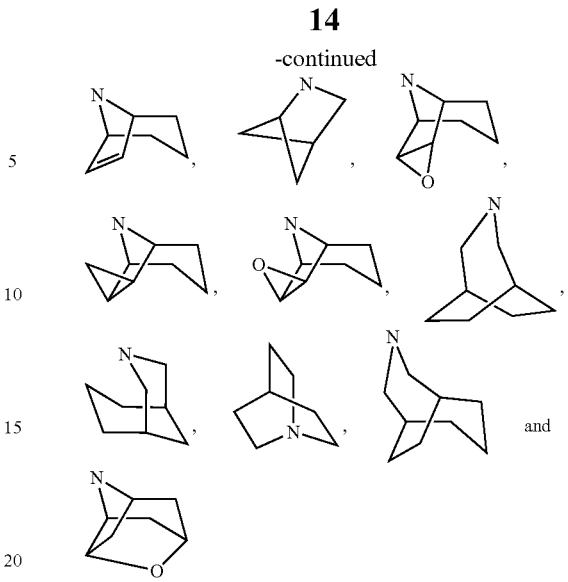

which may optionally be substituted by one or more groups, preferably a group selected from among OH, F, methyl, ethyl, methoxy and —O—COR', where R' denotes a group selected from among $C_1$-$C_4$-alkyl, benzyl and phenylethyl, which may be substituted in each case by hydroxy, hydroxymethyl or methoxy.

The compound of formula 3 is selected from acetone in this preferred process variant according to the invention (reaction 2). It is an aprotic solvent which acts simultaneously as solvent and compound 3. However, another aprotic solvent may additionally be used, such as for example acetonitrile. This is however not preferred.

A particularly mild reaction is possible according to the invention because the catalyst, preferably a catalyst selected from among the tert. alkoxides, is used together with a zeolite. By tert.-alkoxides are meant alkoxides that contain sterically demanding alkyl groups, in which there is at least one quaternary carbon centre. By quaternary carbon centres are meant carbon centres which do not carry a hydrogen atom, but are substituted by 3 to 4 alkyl groups. Carbon centres that are substituted by 3 alkyl groups preferably carry the alkoxide group as the fourth substituent. Suitable tert.-alkoxides are preferably alkali or alkaline earth metal alkoxides, particularly preferably sodium- or potassium-tert.-butoxide or sodium- or potassium-tert.-amylate.

Particularly preferred zeolites are molecular sieves which are selected from among the molecular sieves of a basic nature, consisting of alkali- or alkaline earth-containing alumosilicates, such as sodium- or potassium-containing alumosilicates, preferably molecular sieves with the empirical formula $Na_{12}[(AlO_2)_{12}(SiO_2)_{12}] \times H_2O$ or $Na_{12}Al_{12}Si_{12}O_{36} \times nH_2O$, where n is preferably <6, type 4A molecular sieves being particularly preferred according to the invention.

It has proved to be particularly advantageous if the reaction medium used for the trans-esterification reaction according to the invention is a combination of acetone/tert.-alkoxide or acetonitrile/acetone/tert-alkoxide. The presence of zeolite also prevents the self-condensation reactions of the acetone or acetonitrile that usually take place. Moreover, the use of zeolite effectively deprives the alcohol released of its equilibrium.

The alcohol of formula 4 is variable but in practice is limited to primary or secondary alcohols. For the chemical reaction virtually any primary or secondary alcohol known to the skilled man may be used, as a reaction will take place with any of these alcohols as a result of the shift in the reaction equilibrium caused by removal of the alcohol formed. The reactivity of the alcohols is greatest in primary alcohols. Tertiary alcohols do not participate in this reaction.

The group $R_6$ in the alcohol of formula 4 denotes a substantially freely selectable organic group, which after the reaction constitutes the transesterified group in the 2-hydroxycarboxylic acid ester of formula 5 produced. The desired end product can thus be determined by the choice of alcohol. The organic group $R_6$ may be for example: a branched or unbranched alkyl, a saturated or unsaturated carbocyclic group, heterocyclic group, bicyclic group, tricyclic group, a condensed cyclic system and many others, as well as combinations thereof. Examples of heterocycles are given under the definitions of terms.

Particularly preferred heterocycles which may be used for $R_6$ are selected from pyrrole, pyrroline, pyrrolidine, pyridine, piperidine, morpholine, scopine, N-methylscopinium

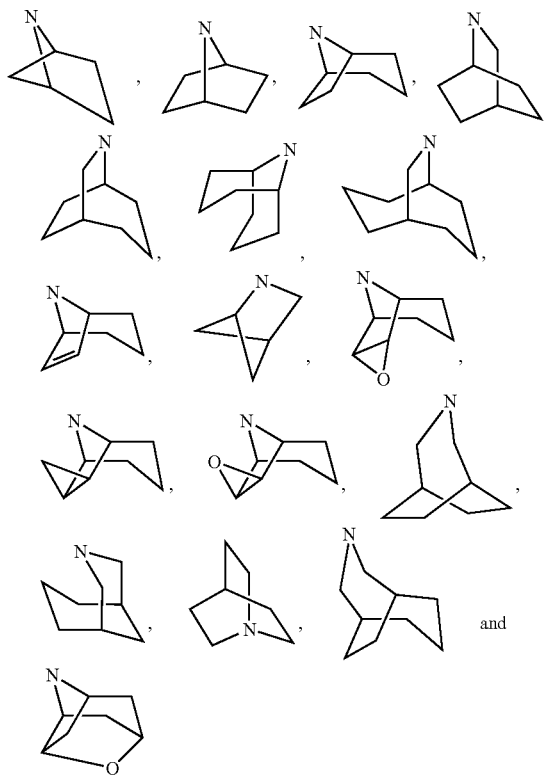

which may optionally be substituted by one or more, preferably one group selected from among OH, F, methyl, ethyl, methoxy and —O—COR', where R' denotes a group selected from among $C_1$-$C_4$-alkyl, benzyl and phenylethyl, which may be substituted in each case by hydroxy, hydroxymethyl or methoxy.

The alcohol is therefore not restricted within the scope of the invention provided that it does not contain a functional group that interferes with the reaction and provided that it is not a tertiary alcohol.

A particular advantage of the new manufacturing process using the catalyst combination consisting of the tert.-alkoxide-impregnated zeolite relates for example to the base-sensitive scopine. The reaction conditions are so gentle that rearrangement into the corresponding scopoline can be avoided.

Instead of the compound of formula 4 $R_6$—OH, a compound of formula 4' $R_6$—$NH_2$ may also be used to prepare a corresponding 2-hydroxycarboxylic acid amide. This applies to reaction 1b and reaction 2 of the invention, while in the event of an amine being used the same solvents and conditions may be used as for the alcohol described. Reaction Scheme 5 for the reaction 1b with the compound of formula 4' $R_6$—$NH_2$ is then obtained as follows:

Reaction Scheme 5

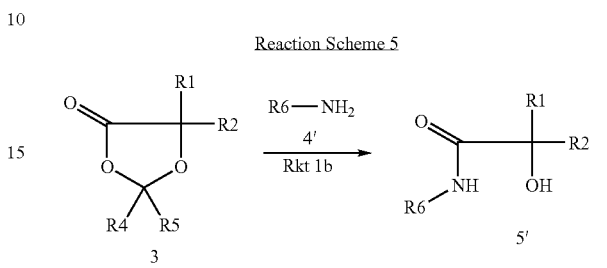

Reaction Scheme 6 for reaction 2 with the compound of formula 4' $R_6$—$NH_2$ is then obtained as follows:

Reaction Scheme 6

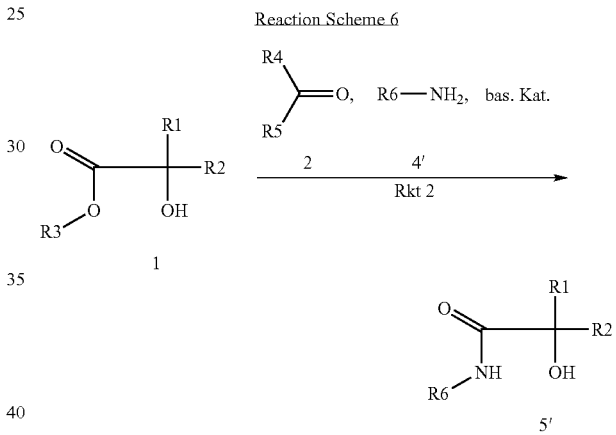

The groups $R_1$ to $R_6$ are defined as hereinbefore.

The reaction of the compound of formula 1 with the compound of formula 2 and the compound of formula 4 or 4' to form the compound of formula 5 or 5' may be carried out, depending on the type of catalyst chosen, at slightly elevated temperature in the range from 25-50° C. The reaction takes place under basic reaction conditions and also functions at ambient temperature (approx. 23° C.) and below. Preferably the reaction takes place under mild conditions at a temperature of about 30° C., particularly preferably in the range from about 0 to about 30° C. The solution obtained is generally stirred until the reaction is complete. After the reaction has ended the compounds of formula 5 or 5' are isolated from the solution. The products obtained may, if necessary, be purified by recrystallisation from a suitable solvent. The product obtained is isolated and optionally dried in vacuo.

The process according to the invention (reaction 2) proceeds selectively, with side reactions largely being suppressed.

The process according to the invention (reaction 2) allows a reaction to take place under very mild conditions, which compared with reactions in highly polar aprotic solvents enters into fewer side reactions. The use of acetone as solvent confers a most particular advantage, as the affinity (intramolecular interaction) of the methanol formed in the chemical equilibrium is very low in relation to other solvents such as DMF or NMP. Thus, endothermy is observed during mixing in acetone, while exothermy occurs when methanol is mixed into DMF. A significantly better yield is obtained compared with the known methods. The reaction may also be used for example for synthesising delicate acid-unstable and/or temperature-sensitive systems.

Particularly preferably, 2-hydroxycarboxylic acid esters, particularly preferably 2-hydroxycarboxylic acid methyl esters, or 2-hydroxycarboxylic acid amides, are prepared by the process according to the invention (reaction 1b, reaction 1a+reaction 1b or reaction 2). These may be obtained in one step while keeping to the basic reaction conditions described, without isolation of the intermediate. (Reaction Ia+reaction Ib=reaction 2)

The transesterification process according to the invention (reaction 2) has proved particularly advantageous when the compound of formula 4 is an alcohol that can be used as a quaternary ammonium salt of hexafluorophosphoric acid, as these salts are soluble in acetone. For example, tiotropium compounds are thus prepared very simply and in good yields.

In another aspect the present invention therefore relates to a process for preparing tiotropium salts of formula 6

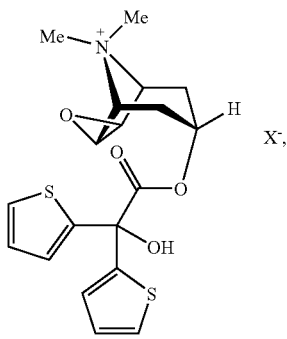

6 wherein

X— may represent an anion with a single negative charge, preferably an anion selected from among the chloride, bromide, iodide, sulphate, phosphate, methanesulphonate, nitrate, maleate, acetate, citrate, fumarate, tartrate, oxalate, succinate, benzoate, p-toluenesulphonate and trifluoromethanesulphonate, wherein a compound of formula 1

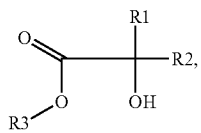

1 wherein $R_1$ and $R_2$ both represent thienyl and $R_3$ denotes a group selected from among methyl, ethyl, propyl, isopropyl, isopropenyl, butyl, —N-succinimide, —N-phthalimide, phenyl, nitrophenyl, fluorophenyl, pentafluorophenyl, vinyl, 2-allyl, is reacted in one step with a compound of formula $R_6$—OH of the chemical formula 7

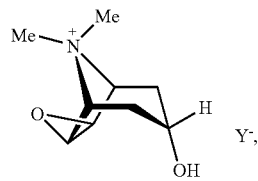

7 wherein $Y^-$ denotes hexafluorophosphate, with a compound of formula 2, preferably from acetone with the addition of a basic catalyst in the form of a tert.-alkoxide in the presence of zeolite, to form a compound of formula 8

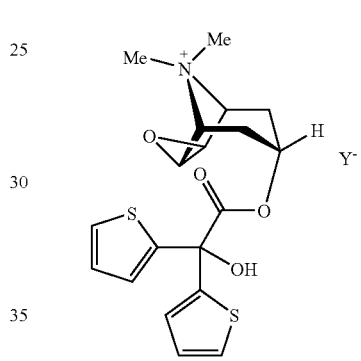

8 wherein the group $Y^-$ has the meaning given hereinbefore, and the compound of formula 8, without being isolated, is converted into the compound of formula 6 by reaction with a salt $Kat^+X^-$, where $Kat^+$ denotes a cation selected from among $Li^+$, $Na^+$, $K^+$, $Mg^{2+}$, $Ca^{2+}$, organic cations with quaternary N (e.g. N,N-dialkylimidazolium, tetraalkylammonium), and $X^-$ may have the meanings given above.

It has proved particularly advantageous, in the working up of the 2-hydroxycarboxylic acid esters prepared, that esters which are simultaneously quaternary ammonium salts of hexafluorophosphates can be converted by means of lithium salts into other salts. In this way the products can be isolated for example by precipitation crystallisation and can then optionally be recrystallised from a suitable solvent.

By quaternary ammonium salts of hexafluorophosphates are meant according to the invention compounds which are hereinafter represented by general formula 9:

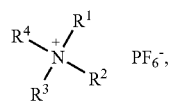

9 wherein $R^1$, $R^2$, $R^3$ and $R^4$ denote the corresponding organic groups. These are prepared for example by reacting ammonium salts of the following general formula 9':

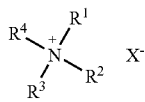

9' in a suitable solvent with a salt $Kat^+PF_6^-$, where $Kat^+$ denotes a cation selected from among $Li^+$, $Na^+$, $K^+$, $Mg^{2+}$, $Ca^{2+}$.

The salts of quaternary ammonium compounds, such as for example those of formula 9', are generally readily soluble in water and alcohol. However, they are distinctly difficult to dissolve in less polar organic solvents such as for example acetone, acetonitrile, hydrocarbons, halohydrocarbons or ethers. The chemical reactions with quaternary ammonium compounds would therefore be restricted in the present instance to reactions in water, alcohol or strongly polar aprotic solvents, such as DMF (dimethylformamide) or NMP (N-methylpyrrolidine). By converting the quaternary ammonium compounds into the corresponding hexafluorophosphates of formula 9, however, less polar aprotic solvents such as acetone, for example, may be used.

Once the hexafluorophosphates have been reacted to form the desired modified ammonium hexafluorophosphates, the hexafluorophosphate can be replaced again by other anions using lithium salts (such as e.g. LiBr), for example.

The advantages of the invention are wide-ranging:

The process according to the invention (reaction 1a) allows a reaction to take place under very mild basic conditions, which result in fewer side reactions and higher yields than reactions in highly polar aprotic solvents. It is possible to synthesise acid- and/or temperature-sensitive compounds.

According to the invention a transesterification may be carried out in one step (reaction 2). It has proved to be particularly advantageous if the reaction medium used for the trans-esterification reaction according to the invention is a combination of acetone/tert.-alkoxide or acetonitrile/acetone/tert-alkoxide. The presence of zeolite also prevents the self-condensation reactions of the acetone or acetonitrile that usually take place. Moreover, the use of zeolite effectively deprives the alcohol released of its equilibrium.

As there are a large number of pharmacologically effective 2-hydroxycarboxylic acid esters, the simple novel manufacturing process for these compounds, and for any precursors they may have in the form of the 1,3-dioxolan-2-ones, is particularly advantageous, especially as the restriction to acid catalysis conditions is removed and the synthesis conditions are very mild.

Besides the 2-hydroxycarboxylic acid esters, the 2-hydroxycarboxylic acid amides may also be prepared according to the invention.

According to the invention 1,3-dioxolan-2-ones of type B have also been identified as anti-cholinergics. In particular, the compounds of formula 610 are highly potent anticholinergically active substances. Moreover, 1,3-dioxolan-2-one compounds that may be prepared according to the invention may be used as starting materials for preparing pharmacologically active carboxylic acid esters, such as e.g. tiotropium bromide. This may be done for example from or via compounds of type A as described above.

The following Examples serve to illustrate methods of synthesis carried out by way of example. They are intended purely as examples of possible procedures without restricting the invention to their contents.

EXAMPLES

Synthesis Examples Relating to Reaction 1a

General Method:

The 2-hydroxycarboxylic acid ester (30 mmol) was dissolved in an excess of the corresponding ketone/aldehyde, then combined with a zeolite of type $Na_{12}Al_{12}Si_{12}O_{36} \times nH_2O$ (pore size 4 Å) (6-24 g) and a catalytic amount of a tert.-alkoxide and stirred at 20-23° C. until the reaction had ended.

The following compounds were obtained analogously to the general method described above:

| | Ex. 1 | Ex. 2 | Ex. 3 | Ex. 4 | Ex. 5 | Ex. 6 | Ex. 7 | Ex. 8 | Ex. 9 | Ex. 10 |
|---|---|---|---|---|---|---|---|---|---|---|
| $R_1$ | H | Ph | 2-thienyl | Ph | Ph | Ph | Ph | Ph | Me | Me |
| $R_2$ | Ph | Ph | 2-thienyl | Ph | H | Ph | Ph | Ph | Me | Me |
| $R_3$ | Me | Me | Me | Me | Me | Me | Me | Me | Me | Me |
| $R_4$ | Me | Me | Me | —$(CH_2)_5$— | —$(CH_2)_5$— | isopropyl | Ph | Ph | —$(CH_2)_5$— | Ph |
| $R_5$ | Me | Me | Me | ring | ring | H | Ph | H | ring | H |
| Yield | 45% | 70.3 | 29.3 | 67.6 | 67.2 | 40.5 | 0 | 0 | 99 | 22 |
| Mp. | 46-47° C. | 38-40° C. | 66-68° C. | oil | oil | oil | — | — | oil, 80% content | oil |

In Example 7 THF was used as solvent.
In Example 9 cyclohexanone was used in an equimolar ratio.
In Examples 1-4 and 6 the product was purified by preparative chromatography with cyclohexane/ethyl acetate = 9:1.
In Example 2 crystals were obtained from water.
In Examples 1 and 3 crystals were obtained from cyclohexane.

Synthesis Example

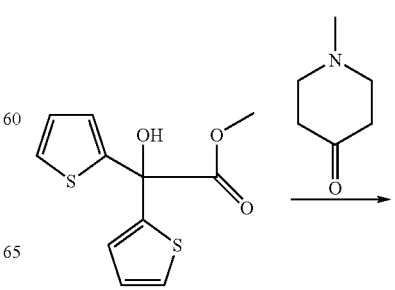

3 g (12 mmol) of methyl dithienylglycolate, 5 g (12 mmol) of N-methyl-4-piperidone, 3 g zeolite of type $Na_{12}Al_{12}Si_{12}O_{36}\times nH_2O$ and 20 mg KOtBu are mixed together. After 15 h at RT 200 ml of toluene are added, the zeolite is filtered off, the filtrate is washed 3× with 500 ml of water and extracted 2× with 50 m of dilute hydrochloric acid. The aqueous extracts are combined with $KHCO_3$ solution and counter-extracted with 200 ml of toluene. After evaporation the mixture is crystallised from diisopropylether, washed and dried.

Yield: 1.3 g (Mp: 102-103° C.) of compound 609.

1.1 g (3.2 mmol) of compound 609 are dissolved in 30 ml acetonitrile and combined with 1.5 mol-eq. (5 mmol) of methyl iodide. After 3 h the mixture is combined with 50 ml ether, filtered off, washed with ether and dried. Yield: 1.5 g (Mp.: 229-230° C.)

Synthesis Examples of Reaction 2

Transesterification without isolation of the intermediate product with direct isolation of the ester
General Method:

An acetone solution of 0.12 mol carboxylic acid ester and 0.1 mol alcohol is combined with 90 g of a zeolite of type $Na_{12}Al_{12}Si_{12}O_{36}\times n\ H_2O$ (type 4A) and 1 mmol of a tertiary alkoxide and stirred at temperatures in the range from 0-30° C. After chemical equilibrium has been reached, the solid fraction is filtered off and the filtrate is worked up.

For esters which are simultaneously quaternary ammonium salts of hexafluorophosphates, the bromide is isolated by the addition of a lithium bromide solution (8.7 g LiBr in 100 ml acetone) by precipitation crystallisation and then recrystallised from methanol.

Synthesis Examples

Example 1

Preparation of 9-methyl-3-oxa-9-aza-tricyclo[3.3.1.0$^{2,4}$]non-7-yl hydroxy-thiophen-2-yl-thiophen-3-yl-acetate from scopine (9-methyl-3-oxa-9-aza-tricyclo[3.3.1.0$^{2,4}$]nonan-7-ol) and methyl dithienylglycolate Yield: 20% (HPLC surface), identity determined by RRT (with comparison substance) by HPLC
Particular advantage: the scopine is not rearranged to form scopoline under these conditions.
By introducing methyl bromide, the corresponding quaternary ammonium bromide is obtained, which is filtered off and recrystallised from water.
Yield: 10% (not optimised)

Example 2

Preparation of 3-(2-hydroxy-2-thiophen-2-yl-2-thiophen-3-yl-acetoxy)-8,8-dimethyl-8-azonia-bicyclo[3.2.1]octane as bromide N-methyltropinium $PF_6$ and methyl dithienylglycolate are dissolved in acetone and treated in accordance with the general method.
Identity determined by RRT (with comparison substance) by TLC Example 3

Preparation of 7-(2-hydroxy-2,2-diphenyl-acetoxy)-9,9-dimethyl-3-oxa-9-azonia-tricyclo-[3.3.1.0$^{2,4}$]nonane Methyl benzilate and N-methylscopinium hexafluorophosphate are dissolved in acetone and treated in accordance with the general method. After the end of the reaction the product is crystallised by the addition of an acetonic lithium bromide solution and recrystallised from methanol.

a) Bromide: yield (not optimised) 57%
Mp.: 178-182° C., identity confirmed by RRT (with comparison substance) by TLC
b) Hexafluorophosphate: by precipitation with sodium hexafluorophosphate in water from the bromide: 82%, Mp.: 178-182° C., identity confirmed by RRT (with comparison substance) by TLC Example 4

Preparation of 9,9-dimethyl-7-(9-hydroxy-9H-fluorene-9-carbonyloxy)-3-oxa-9-azonium-tricyclo[3.3.1.0$^{2,4}$]nonane bromide Methyl 9-hydroxy-fluorene-9-carboxylate and N-methylscopinium hexafluorophosphate are dissolved in acetone and treated in accordance with the general method. After the end of the reaction the product is crystallised by the addition of an acetonic lithium bromide solution and recrystallised from methanol.

a) Bromide: yield (not optimised) 46%
Mp.: 238-241° C.
b) Hexafluorophosphate: by precipitation with sodium hexafluorophosphate in water from the bromide: 70%, Mp.: 265-271° C. (decomposition)

The invention claimed is:
1. A process for preparing 1,3-dioxolan-2-one of formula 3 wherein
$R_1$ and $R_2$ each independently of one another represent hydrogen or an aryl or heteroaryl group, while the aryl or heteroaryl group may optionally be mono- or polysubstituted in each case;

$R_4$ and $R_5$ are each independently of one another selected from among hydrogen, $C_1$-$C_6$-alkyl, or $R_4$ and $R_5$ together form a saturated or mono- or polyunsaturated carbocyclic or heterocyclic ring which may contain one or more heteroatoms, selected from S, N or O, each of which may optionally be mono- or polysubstituted independently of one another, while $R_4$ and $R_5$ cannot both simultaneously be hydrogen;

comprising reacting in one step a 2-hydroxycarboxylic acid ester of formula 1

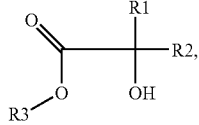

1 wherein
$R_1$ and $R_2$ are as hereinbefore defined and
$R_3$ denotes methyl, ethyl, propyl, isopropyl, isopropenyl, butyl, N-succinimide, N-phthalimide, phenyl, nitrophenyl, fluorophenyl, pentafluorophenyl, vinyl, 2-allyl,
in a suitable solvent with the addition of a suitable tert-alkoxide basic catalyst, in the presence of zeolite, with a compound of formula 2

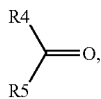

2 wherein $R_4$ and $R_5$ are as hereinbefore defined.

2. The process according to claim 1, wherein the reaction is carried out at a temperature in the range from about 0 to about 30° C.

3. The process according to claim 1, wherein the zeolite is selected from among the alkali- or alkaline earth-containing alumosilicates.

4. The process according to claim 1, wherein the solvent is a ketone, nitrile or heteroaromatic solvent.

5. The process according to claim 1, wherein $R_3$ is selected from among methyl, ethyl, propyl and butyl.

6. The process according to claim 1, wherein $R_1$ and $R_2$ are each selected from among a heteroaryl group each optionally mono- or polysubstituted by halogen atoms, —CN, $C_1$-$C_4$-alkyl, $C_1$-$C_4$-alkoxy, hydroxy, or $CF_3$.

7. The process according to claim 1, wherein the same heteroaryl group is used for $R_1$ and $R_2$.

8. The process according to claim 1, wherein the thienyl group is used in each case for $R_1$ and $R_2$.

9. The process according to claim 1, wherein $R_4$ and $R_5$ are independently selected from $C_1$-$C_6$-alkyl.

10. The process according to claim 1, wherein $R_4$ and $R_5$ together form a saturated carbocyclic or heterocyclic ring which is in each case optionally mono- or polysubstituted by halogen atoms, —CN, $C_1$-$C_4$-alkyl, $C_1$-$C_4$-alkoxy, hydroxy, $CF_3$ and —O—COR', where R' denotes a group selected from among $C_1$-$C_4$-alkyl, benzyl and phenylethyl, which may be substituted in each case by hydroxy, hydroxymethyl or methoxy.

11. The process according to claim 1, wherein $R_4$ and $R_5$ together with a nitrogen atom form a heterocyclic ring selected from pyrrole, pyrroline, pyrrolidine, pyridine, piperidine, morpholine,

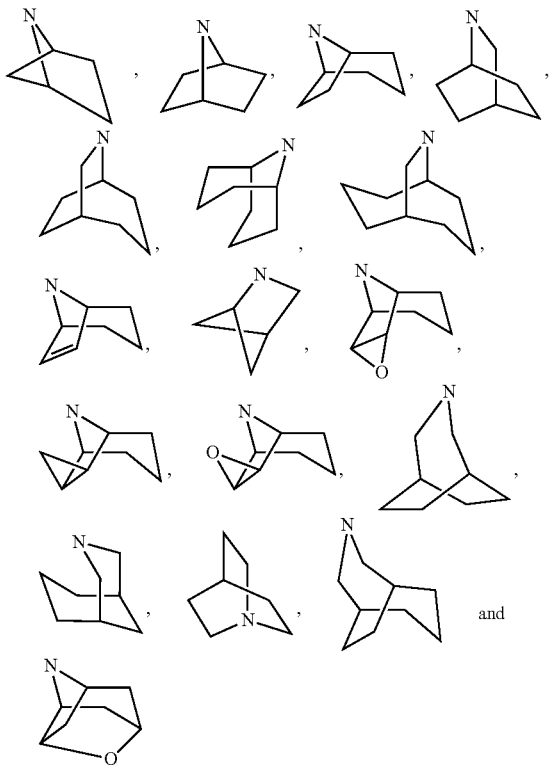

which may optionally be substituted by one or more groups, preferably a group selected from among OH, F, methyl, ethyl, methoxy and —O—COR', where R' denotes a group selected from among $C_1$-$C_4$-alkyl, benzyl and phenylethyl, which may be substituted in each case by hydroxy, hydroxymethyl or methoxy.

12. The process according to claim 1, wherein an acid-sensitive 2-hydroxycarboxylic acid ester is present as starting material and/or as end product.

13. The process according to claim 1, wherein the catalyst is selected from the group consisting of alkali or alkaline earth metal tert-alkoxides.

14. The process according to claim 13, wherein the alkali or alkaline earth metal tert-alkoxide is sodium-tert-butoxide, potassium-tert-butoxide, sodium-tert-amylate or potassium-tert-amylate.

15. The process according to claim 3, wherein the alumosilicate is a sodium-containing alumosilicate, a potassium-containing alumosilicate, or a molecular sieve with the empirical formula $Na_{12}[(AlO_2)_{12}(SiO_2)_{12}] \times H_2O$ or $Na_{12}Al_{12}Si_{12}O_{36} \times nH_2O$, wherein n is less than 6.

16. The process according to claim 1, wherein the solvent is acetone, pyridine or acetonitrile.

17. The process according to claim 9, wherein each $R_4$ and $R_5$ is methyl or ethyl.

18. The process according to claim 1, wherein $R_4$ and $R_5$ together form a pyridinyl ring.

* * * * *